US00PP24586P2

(12) United States Plant Patent
Wood

(10) Patent No.: US PP24,586 P2
(45) Date of Patent: Jul. 1, 2014

(54) BARBERRY PLANT NAMED 'CELESTE'

(50) Latin Name: *Berberis thunbergii*
Varietal Denomination: Celeste

(75) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 82 days.

(21) Appl. No.: 13/573,165

(22) Filed: Aug. 27, 2012

(51) Int. Cl.
*A01H 5/00* (2006.01)

(52) U.S. Cl.
USPC ..... Plt./241

(58) Field of Classification Search
CPC ..... A01H 5/00
USPC ..... Plt./241
See application file for complete search history.

*Primary Examiner* — Susan McCormick Ewoldt
(74) *Attorney, Agent, or Firm* — C. A. Whealy

(57) ABSTRACT

A new and distinct cultivar of Barberry plant named 'Celeste', characterized by its upright, outwardly spreading and mounding plant habit; vigorous growth habit; freely branching habit; leaves that are dark greyed purple to dark greyed orange in color; good garden performance; and resistance to Black Stem Rust.

2 Drawing Sheets

Botanical designation: *Berberis thunbergii.*
Cultivar denomination: 'CELESTE'.

BACKGROUND OF THE INVENTION

The present invention relates to a new and distinct cultivar of Barberry plant, botanically known as *Berberis thunbergii* and hereinafter referred to by the name 'Celeste'.

The new Barberry plant is a product of a planned breeding program conducted by the Inventor in Grand Haven, Mich. The objective of the breeding program was to develop new unique Barberry plants with attractive foliage, improved stress tolerance and resistance to Black Stem Rust (*Puccinia graminis*).

The new Barberry plant originated from an open-pollination in June, 2003 of Barberry *thunbergii* 'Rose Glow', not patented, as the female, or seed parent and an unknown selection of Barberry *thunbergii* as the male, or pollen, parent. The new Barberry plant was discovered and selected by the Inventor since June, 2006 as a single plant within the progeny of the stated open-pollination in a controlled environment in Grand Haven, Mich.

Asexual reproduction of the new Barberry plant by softwood cuttings in a controlled greenhouse environment in Grand Haven, Mich. since June, 2006 has shown that the unique features of this new Barberry plant are stable and reproduced true to type in successive generations of asexual reproduction.

SUMMARY OF THE INVENTION

Plants of the new Barberry have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Celeste'.

These characteristics in combination distinguish 'Celeste' as a new and distinct Barberry plant:

1. Upright, outwardly spreading and mounding plant habit.
2. Vigorous growth habit.
3. Freely branching habit.
4. Leaves that are dark greyed purple to dark greyed orange in color.
5. Good garden performance.
6. Resistance to Black Stem Rust.

Plants of the new Barberry can be compared to plants of the female parent, 'Rose Glow'. Plants of the new Barberry differ primarily from plants of 'Rose Glow' in leaf color as plants of 'Rose Glow' have pink and burgundy bi-colored leaves.

Plants of the new Barberry can be compared to plants of the *Berberis thunbergii* 'Atropurpurea', not patented. In side-by-side comparisons conducted in Grand Haven, Mich., plants of the new Barberry differed primarily from plants of 'Atropurpurea' in the following characteristics:

1. Plants of the new Barberry grew more uniformly than plants of 'Atropurpurea'.
2. Plants of the new Barberry and 'Atropurpurea' differed in leaf color as plants of 'Atropurpurea' had red purple-colored leaves.
3. Plants of the new Barberry were resistant to Black Stem Rust whereas plants of 'Atropurpurea' were not resistant to Black Stem Rust.

BRIEF DESCRIPTION OF THE PHOTOGRAPHS

The accompanying colored photographs illustrate the overall appearance of the new Barberry plant showing the colors as true as it is reasonably possible to obtain in colored reproductions of this type. Colors in the photographs may differ slightly from the color values cited in the detailed botanical description which accurately describe the colors of the new Barberry plant.

The photograph on the first sheet is a side perspective view of a typical plant of 'Celeste' grown in an outdoor nursery.

The photograph on the second sheet is a close-up view of a typical plant of 'Celeste'.

DETAILED BOTANICAL DESCRIPTION

The aforementioned photographs and following observations, measurements and values describe plants grown during the spring and summer in an outdoor nursery in Grand Haven, Mich. and under cultural practices which closely approximate commercial Barberry production. Plants used for the photographs and description were five years old. In the following detailed description, color references are made to The Royal Horticultural Society Colour Chart, 1995 Edition, except where general terms of ordinary dictionary significance are used.

Botanical classification: *Berberis thunbergii* 'Celeste'.

Parentage:

*Female, or seed, parent.*—Barberry *thunbergii* 'Rose Glow', not patented.

*Male, or pollen, parent.*—Unknown selection of Barberry *thunbergii,* not patented.

Propagation:

*Type.*—By softwood cuttings.

*Time to initiate roots, summer.*—About 70 days at 20° C.

*Time to produce a rooted young plant, summer.*—About one year at 20° C.

*Root description.*—Fine to medium; somewhat fleshy and fibrous; yellow in color.

*Rooting habit.*—Freely branching; dense.

Plant description:

*Plant form and growth habit.*—Perennial shrub; upright, outwardly spreading and mounding plant habit; rapid growth rate and vigorous growth habit; freely branching habit with about 72 lateral branches developing per plant.

*Plant height.*—About 60 cm.

*Plant diameter* (*area of spread*).—About 70 cm.

Lateral branch description:

*Length.*—About 20 cm.

*Diameter.*—About 2 mm.

*Internode length.*—About 1.3 cm.

*Aspect.*—Erect to outwardly spreading.

*Strength.*—Strong, flexible.

*Texture.*—Smooth, glabrous.

*Color.*—Close to 145A; at the nodes, close to 46A.

*Thorns.*—Quantity: One thorn developing at each node. Length: About 1.3 cm. Width: About 0.5 mm. Color: Towards the apex, close to 187A; towards the base, close to 13A.

Foliage description:

*Arrangement.*—Alternate or whorled; simple.

*Length.*—About 2 cm.

*Width.*—About 1.1 cm.

*Shape.*—Roughly spatulate.

*Apex.*—Obtuse.

*Base.*—Attenuate.

*Margin.*—Entire.

*Texture, upper and lower surfaces.*—Smooth, glabrous.

*Venation pattern.*—Pinnate.

*Color.*—Developing leaves, upper surface: Close to 187A. Developing leaves, lower surface: Close to 187B. Fully expanded leaves, upper surface: Close to 144A heavily tinted with close to 175A; venation, close to 144A heavily tinted with close to 175A. Fully expanded leaves, lower surface: Close to 138B; venation, close to 138B.

*Petiole.*—Length: About 6 mm. Diameter: About 3 mm. Texture, upper and lower surfaces: Smooth, glabrous. Color, upper and lower surfaces: Close to 175A.

Flower description: Flower initiation and development has not been observed on plants of the new Barberry.

Garden performance: Plants of the new Barberry have been observed to have excellent garden performance and to tolerate rain, wind and temperatures ranging from about −30° C. to about 32° C.

Pathogen & pest resistance: Plants of the new Barberry have been observed to be resistant to Black Stem Rust (*Puccinia graminis*). Plants of the new Barberry have not been shown to be resistant to pests and other pathogens common to Barberry plants.

It is claimed:

1. A new and distinct Barberry plant named 'Celeste' as illustrated and described.

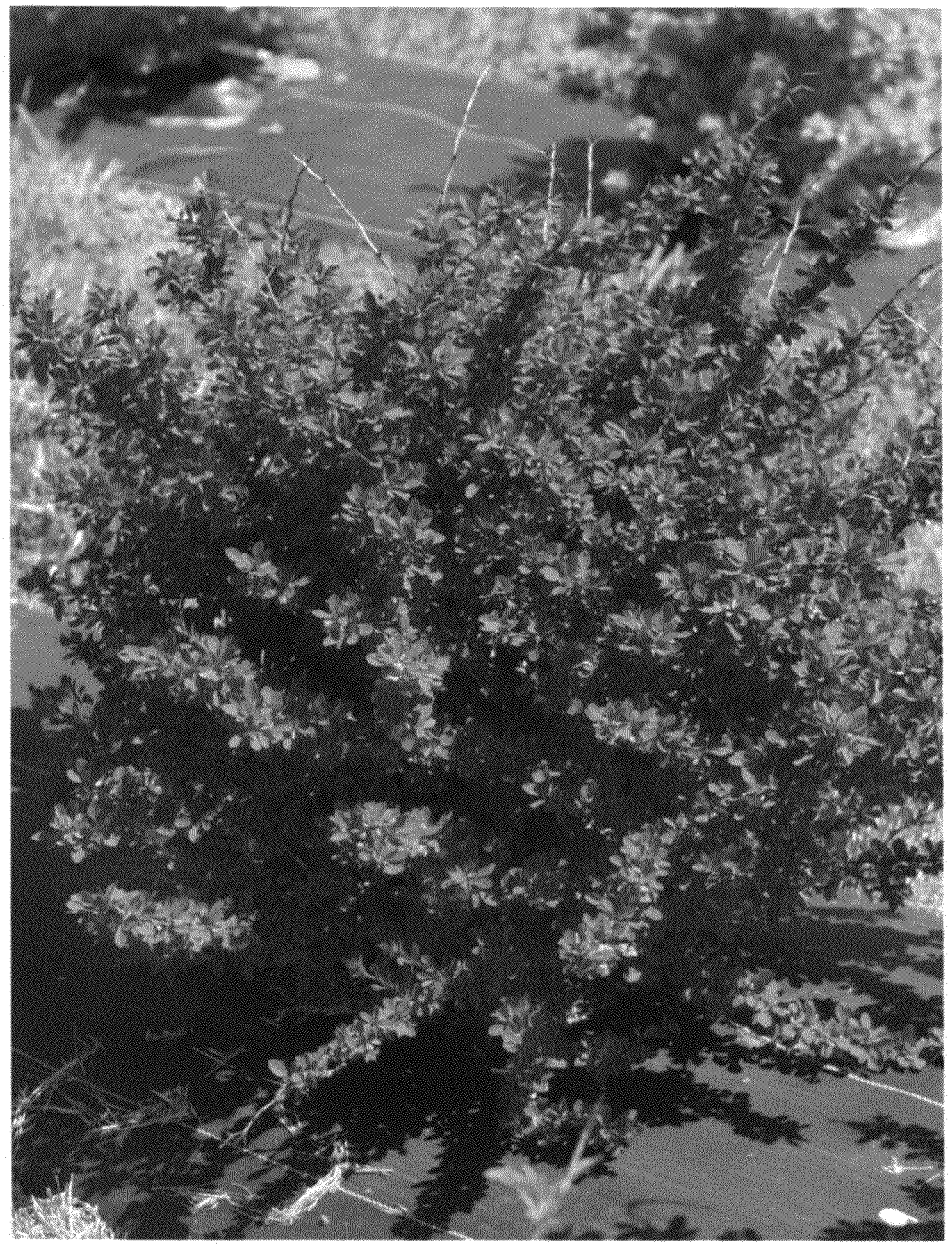

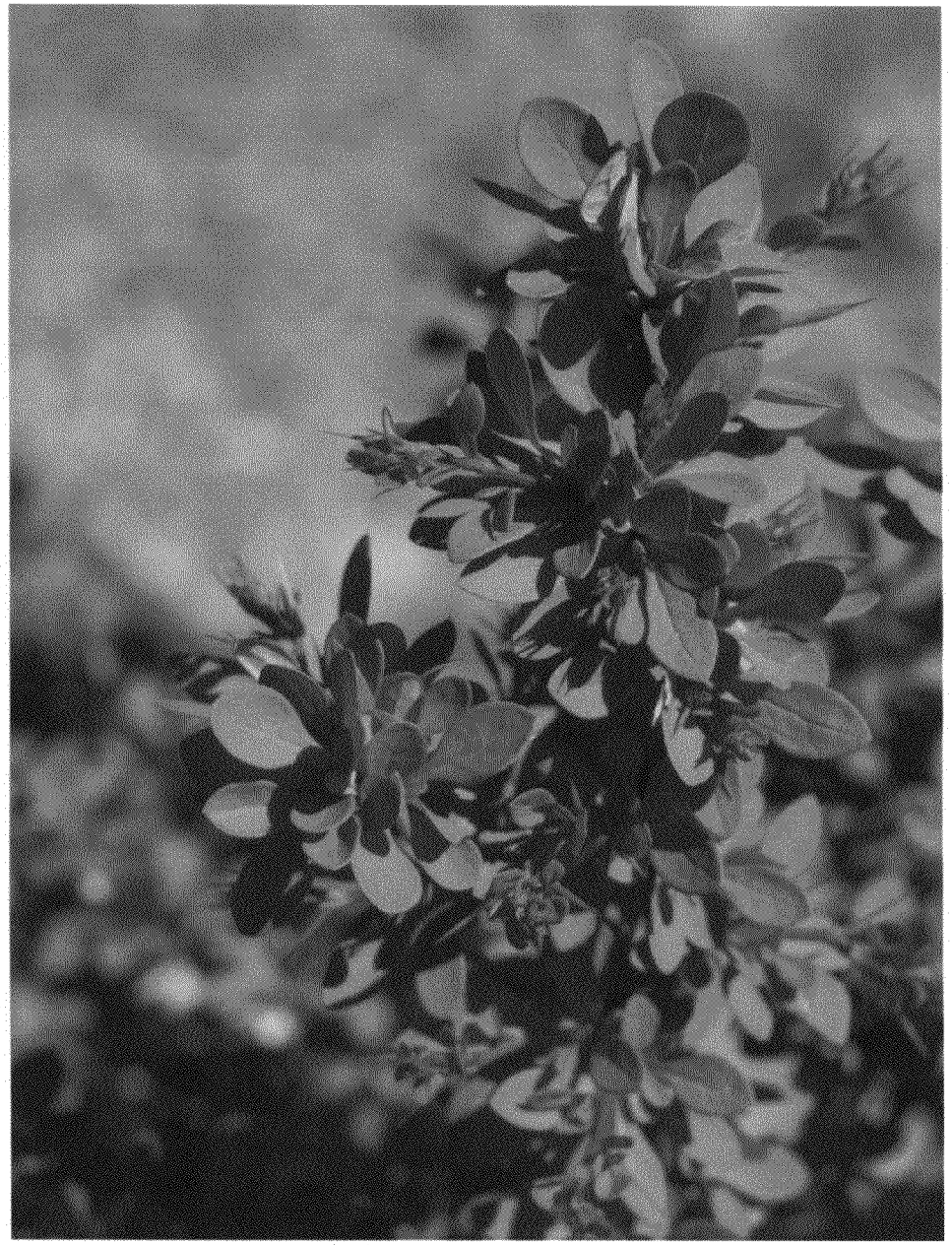

* * * * *